US006477424B1

(12) United States Patent
Thompson et al.

(10) Patent No.: US 6,477,424 B1
(45) Date of Patent: Nov. 5, 2002

(54) MEDICAL MANAGEMENT SYSTEM INTEGRATED PROGRAMMING APPARATUS FOR COMMUNICATION WITH AN IMPLANTABLE MEDICAL DEVICE

(75) Inventors: David L. Thompson, Fridley, MN (US); Steven D. Goedeke, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/322,560

(22) Filed: May 28, 1999

Related U.S. Application Data

(60) Provisional application No. 60/089,868, filed on Jun. 19, 1998.

(51) Int. Cl.[7] .................................................. A61N 1/08
(52) U.S. Cl. .......................................... 607/60; 607/32
(58) Field of Search ............................... 607/27, 32, 60; 600/300, 301, 510

(56) References Cited

U.S. PATENT DOCUMENTS

| 4,379,459 | A | 4/1983 | Stein |
|---|---|---|---|
| 4,476,868 | A | 10/1984 | Thompson |
| 4,556,063 | A | 12/1985 | Thompson et al. |
| 4,821,723 | A | 4/1989 | Baker, Jr. et al. |
| 5,127,404 | A | 7/1992 | Wyborney et al. |
| 5,131,388 | A | 7/1992 | Pless et al. |
| 5,144,949 | A | 9/1992 | Olson |
| 5,158,078 | A | 10/1992 | Bennett et al. |

(List continued on next page.)

OTHER PUBLICATIONS

Product Literature from Hewlett Packard, "HP M1275A Component Transport System—Technical Information", 4 pgs, Printed in U.S.A. (Feb. 1995), No. 5963–3379E (1995).
Product Literature from Hewlett Packard, "HP M1275A Component Transport System Mountin g Options—Technical Data", Cardiac Services: Data Sheet HP Viridia Patient Monitoring System, 4 pgs, Printed in U.S.A. (Sep. 1997), No. 5966–3376E (1992, 1997).

(List continued on next page.)

Primary Examiner—Jeffrey R. Jastrzab
(74) Attorney, Agent, or Firm—Girma Wolde-Michael (57) ABSTRACT

An implantable medical device communication system includes an implantable medical device, a medical information management system, and a module interface apparatus for facilitating communication therebetween. The implantable medical device includes transmitter/receiver circuitry coupled to a device antenna. The medical information management system includes at least a computer processing unit and a display unit. The module interface apparatus includes interface receiver/transmitter circuitry coupled to an interface antenna to communicate with the device transmitter/receiver circuitry via the device antenna. Further, the module interface apparatus includes interface circuitry operable to adapt data (e.g., programming commands) received from the medical information management system for transmittal to the implantable medical device and adapt data received from the implantable medical device (e.g., device data including operational data, physiological parameter data, analyzed data, diagnostic data, etc.) such as to communicate such information to:the medical information management system.

16 Claims, 7 Drawing Sheets

U.S. PATENT DOCUMENTS

| | | |
|---|---|---|
| 5,168,871 A | 12/1992 | Grevious |
| 5,199,428 A | 4/1993 | Obel et al. |
| 5,207,218 A | 5/1993 | Carpentier et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| H1347 H | 8/1994 | Greeninger et al. |
| 5,342,408 A | 8/1994 | De Coriolis |
| 5,345,362 A | 9/1994 | Winkler et al. |
| 5,354,316 A | 10/1994 | Keimel |
| 5,372,607 A | 12/1994 | Stone et al. |
| 5,417,222 A | 5/1995 | Dempsey et al. |
| 5,520,191 A | 5/1996 | Karlsson et al. |
| 5,527,348 A | 6/1996 | Winkler et al. |
| 5,545,186 A | 8/1996 | Olson et al. |
| 5,579,775 A | 12/1996 | Dempsey et al. |
| 5,626,630 A * | 5/1997 | Markowitz et al. ........... 607/32 |
| 5,683,432 A | 11/1997 | Goedeke et al. |
| 5,687,734 A | 11/1997 | Dempsey et al. |
| 6,150,951 A * | 11/2000 | Olejniczak ................... 607/60 |

OTHER PUBLICATIONS

Product Literature from Hewlett Packard, "HP M1165A/66A/67A Viridia CMS Release G—Technical Data Sheet", 20 pgs., internet site: http//www.cardiac–services.com/ireland/hp_viridia.html, accessed May 12, 1999.

Product Literature from Probe, "Plugged in Introducing the HP OmniCare CMS Model 24", 3 pgs, internet site: http//interactive.medical.hp.com/mpgcsd/probe/2.2.1.3.html, accessed May 12, 1999.

* cited by examiner

MEDICAL MANAGEMENT SYSTEM INTEGRATED PROGRAMMING APPARATUS FOR COMMUNICATION WITH AN IMPLANTABLE MEDICAL DEVICE

CROSS-REFERENCE TO RELATION APPLICATIONS

This application claims the benefit of U.S. Provisional Application No. 60/089,868, filed 19 Jun. 1998.

FIELD OF THE INVENTION

The present invention relates to implantable medical devices. More particularly, the present invention pertains to apparatus and methods for use in the communication of information to/from an implantable medical device, e.g., programming commands, diagnostic information, etc.

BACKGROUND OF THE INVENTION

Communication systems employing radio frequency (RF) transmitters and receivers are common. One application of such communication systems is in the field of body implantable medical devices, such as pacemakers, defibrillators, neural stimulators, and the like. RF communication is used to establish "downlink" telemetry channels, in which operational data and commands are transmitted from an external programming unit transmitter to a receiver in an implanted medical device, and/or is used to establish "uplink" telemetry channels, in which information is transmitted from the implanted medical device's transmitter to a receiver in the external unit.

A specific example of a particular component of a telemetry system for implantable medical devices is the Medtronic Model 9790 programmer, commercially available from Medtronic, Inc., the assignee of the present invention. The Model 9790 programmer, with appropriate software modules, can be used to communicate (both uplink and downlink) with numerous body implanted devices manufactured by Medtronic, Inc.

Conventionally, as exemplified by the Model 9790 programmer in conjunction with a Medtronic implantable medical device (e.g., a pacemaker), an antenna in the form of a multiple turn wire coil is disposed within the hermetic enclosure of the implanted medical device. Downlink RF signals transmitted to the implanted device from an external unit induce a current in the coil antenna, and this current is amplified and applied to a receiver input for demodulation and extraction of the information content of the RF signal. Similarly, for uplink communication, electrical current applied directly to the implanted coil antenna, cause RF electromagnetic signals to be generated. Such signals can be received by a corresponding antenna associated with the external unit.

For various reasons, including the desire to minimize the necessary strength of both uplink and downlink telemetry signals in implantable medical device systems, the external unit, e.g., programmer, of an implantable medical device system typically includes a relatively small, hand-held programming head containing an external antenna, so that this programming head can be placed directly over the implant site of the implanted device. This minimizes the distance between the implanted antenna associated with the implanted device and the external antenna associated with the programmer. For example, the head is typically connected to a larger base unit of a programmer via a multiple conductor cable. The aforementioned Model 9790 is one example of an implantable device programmer having this configuration. The Model 9790 is described in further detail in U.S. Pat. No. 5,345,362 to Winkler et al., entitled "Portable Computer Apparatus With Articulating Display Panel." Further, a programming head and cable for use with such an implanted device programmer is described in U.S. Pat. No. 5,527,348 to Winkler et al., entitled "Magnetically Permeable E-Shield And A Method Of Connection Thereto."

Various communication systems provide the necessary uplink and downlink communication channels between an external unit, e.g., programmer and the implanted medical device. However, some communication systems do not require the use of a hand-held programming head containing the external antenna. For example, such a communication system is described in U.S. Pat. No. 5,683,432 to Goedeke et al., entitled, "Adaptive, Performance-Optimizing Communication System For Communicating With An Implanted Medical Device."

As the complexity of implantable medical devices increases over time, communication systems for enabling such implantable medical devices to communicate with external communication devices, e.g., programmers, has become more important. For example, it is desirable for a physician to non-invasively exercise some amount of control over the implanted medical device, e.g., to turn the device on or off after implantation, to adjust various parameters of the implantable medical device after implantation, etc.

Further, as implantable medical devices include more advanced features, it is typically necessary to convey correspondingly more information to the implantable medical device relating to the selection and control of such advanced features. For example, not only is a pacemaker selectively operable in various pacing modes, it is desirable that the physician be able to non-invasively select a mode of operation. Further, for example, if a pacemaker is capable of pacing at various rates or of delivering stimulating pulses of varying energy levels, it is desirable that the physician be able to select, on a patient-by-patient basis, appropriate values for such variable operational parameters. Various types of information are conveyed to implanted medical devices by telemetry systems. For example, information conveyed to pacemakers may include, but is clearly not limited to, pacing modes, multiple rate response settings, electrode polarity, maximum and minimum pacing rates, output energy such as output pulse width and/or output current, sense amplifier sensitivity, refractory periods, and calibration information.

Not only has the complexity of implantable medical devices led to the need to convey correspondingly more information to the implantable medical device, but it has also become desirable to enable the implanted medical device to communicate a large amount of information outside of the patient to an external communication device, e.g., programmer. For example, for diagnostic purposes, it is desirable for the implanted device to be able to provide information regarding its operational status to the physician. Further, various implantable medical devices are available which transmit information to an external communication device such as digitized physiological parameter signals, e.g., ECG, for display, storage, and/or analysis by the external communication unit. Generally, such information conveyed from the implanted medical device includes any type of diagnostic information and/or information relating to the physiological parameters of the patient in which the device is implanted.

Substantial technological improvements in the field of electronics over the past years has enabled computer equipment manufacturers to provide powerful, fully-featured computers that are compact and portable. Such computers have proven to be extremely popular and a wide variety of such computers are known and commercially available. A portable computer apparatus typically has at least a subset of the following components: a housing for containing the computer circuitry and other electronic components; a power source (e.g., a battery or a cable for connecting the apparatus to a source of power); a user input apparatus (e.g., an alphanumeric keyboard or a mouse); and an output means (e.g., a text and/or graphic display and/or a printer) for communicating information to the user. In addition, portable computer equipment will frequently be equipped with data storage devices, such as a floppy disk drive or a hard disk drive.

Conventional programmers have generally been "standalone" devices and portable like that of portable computer apparatus as described above. For example, several available programmers include the Medtronic Model 9710 for which some further detail is described in U.S. Pat. No. 5,168,871 to Grevious, entitled "Method And Apparatus For Processing Quasi-Transient Telemetry Signals In Noisy Environments"; Medtronic Model No. 9760 for which some further detail is described in U.S. Registration No. H1347 to Greeninger et al., entitled "Audio Feedback For Implantable Medical Device Instruments;" and Medtronic Model No. 9790 for which some further detail is described in U.S. Pat. No. 5,372,607 to Stone et al., entitled, "Method And Apparatus For Monitoring Pacemaker Intervals." Generally, such standalone devices are portable, as described above, completely self-contained devices that require the use of paper, cable connections, diskettes, or an infrared (IR) link to generate archival data.

Such conventional standalone programming apparatus have some shortcomings. For example, such standalone devices are generally time consuming to design and develop. Further, from a computer hardware perspective, such programming apparatus must continually be updated and upgraded to keep up with current hardware technology improvements, e.g., new processors, electrical circuitry, etc. As such, these programmers are generally relatively expensive.

In addition, conventional programming apparatus generally require that an extensive amount of diagnostic data be generated which is reviewed and integrated into a patient's file. However, such data is generally required to be manually entered by either or all of the following methods including handwritten entry, keyboard entry, and printing of forms and then assembly of them into the patient's file. This may lead to errors during the transfer of such data and limit the amount of data saved because of time constraints.

Table 1 below lists U.S. Patents relating to various components of implantable medical device communication systems.

TABLE 1

| U.S. Pat. No. | Inventor(s) | Issue Date |
| --- | --- | --- |
| 5,527,348 | Winkler et al. | 18 June 1996 |
| 5,372,607 | Stone et al. | 13 December 1994 |
| H1347 | Greeninger et al. | 2 August 1994 |
| 5,683,432 | Goedeke et al. | 4 November 1997 |
| 5,168,871 | Grevious | 8 December 1998 |

All references listed in Table 1, and elsewhere herein, are incorporated by reference in their respective entireties. As those of ordinary skill in the art will appreciate readily upon reading the Summary of the Invention, Detailed Description of the Embodiments, and claims set forth below, at least some of the apparatus and methods disclosed in the references of Table 1 and elsewhere herein may be modified advantageously by using the teachings of the present invention. However, the listing of any such references in Table 1, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to programming apparatus. One of such problems involves the use of standalone programmers. For example, with the use of standalone programmers, it is generally required to continually update hardware with the development of new technology. Further, design and development of standalone programmers is relatively expensive. Yet further, data generated by standalone programmers must generally be reviewed and integrated into a patient's file. Due to the standalone nature of the programmers, it is sometimes necessary to manually enter such data into a patient's file. Generally, such manual entering leads to undesirable errors in the patient's file and limitation as to the amount of data saved.

In comparison to known programming apparatus, various embodiments of the present invention may provide one or more of the following advantages. For example, expensive hardware upgrading is reduced. Further, data generated by an implantable medical device may be integrated more readily and more comprehensively into a patient's file. As such, errors due to manual entry may be eliminated. Further, for example, the use of an already existing infrastructure into which a programming apparatus according to the present invention is integrated, allows the programming apparatus to "piggyback" on the natural progression of the infrastructure, e.g., hospital/clinic capital upgrades. Such a piggyback arrangement would reduce the need to continually upgrade operating systems, print options, database management, and connectivity requirements provided by the existing infrastructure. Further, it would reduce capital investment required by entities (e.g., hospitals, clinics, etc.) due to the already existing infrastructure to facilitate communication with the implantable medical device.

Some embodiments of the present invention include one or more of the following features: a module interface apparatus for facilitating communication between an implantable medical device and a medical information management system (e.g., a currently existing infrastructure of a medical facility computer communication network); a module interface apparatus including at least one of an interface receiver and an interface transmitter coupled to an interface antenna to communicate with at least one of a device transmitter and a device receiver of an implantable medical device; a module interface apparatus that includes interface circuitry operable to adapt data received from the medical information management system for provision to the interface transmitter to communicate such information to the implantable medical device; a module interface apparatus that includes interface circuitry to adapt data received from the interface receiver to communicate such information to a medical information management system; an interface module that includes a module housing which encloses at least one of an interface receiver and an interface transmitter wherein a programming head contains an interface antenna and a cable electrically connects the programming head to the interface module; an interface module that includes a module housing, wherein at least one of the interface receiver and interface transmitter are enclosed within the module housing and further wherein the interface antenna is external to the module housing; an interface module that includes processing circuitry to receive and process information signals from an interface receiver received from a implantable medical device; a plurality of interface modules, wherein each interface module is operable for use in communication of information between an external device corresponding to the interface module and a medical information management system; a medical information management system that includes a battery operable processing unit; a medical information management system that includes a computer network; programming commands provided to the interface module from a medical information management system; diagnostic and/or physiological parameter data provided from an interface module to a medical information management system; a programming method wherein data representing programming commands is received at an interface module, the data is adapted for transmission to the implantable medical device, and the adapted data is transmitted by an interface antenna to the implantable medical device; an implantable medical device uplink communication method wherein data is received from an interface module from a device transmitter of an implantable medical device by an interface antenna, the data received is adapted for provision to a medical information management system, and the adapted data is provided to the medical information management system.

The above summary of the present invention is not intended to describe each embodiment of every implementation of the present invention. Advantages, together with a more complete understanding of the invention, will become apparent and appreciated, by referring to the following detailed description and claims taken in conjunction with the accompanying drawings.

DETAILED DESCRIPTION OF THE EMBODIMENTS

Figure 1:
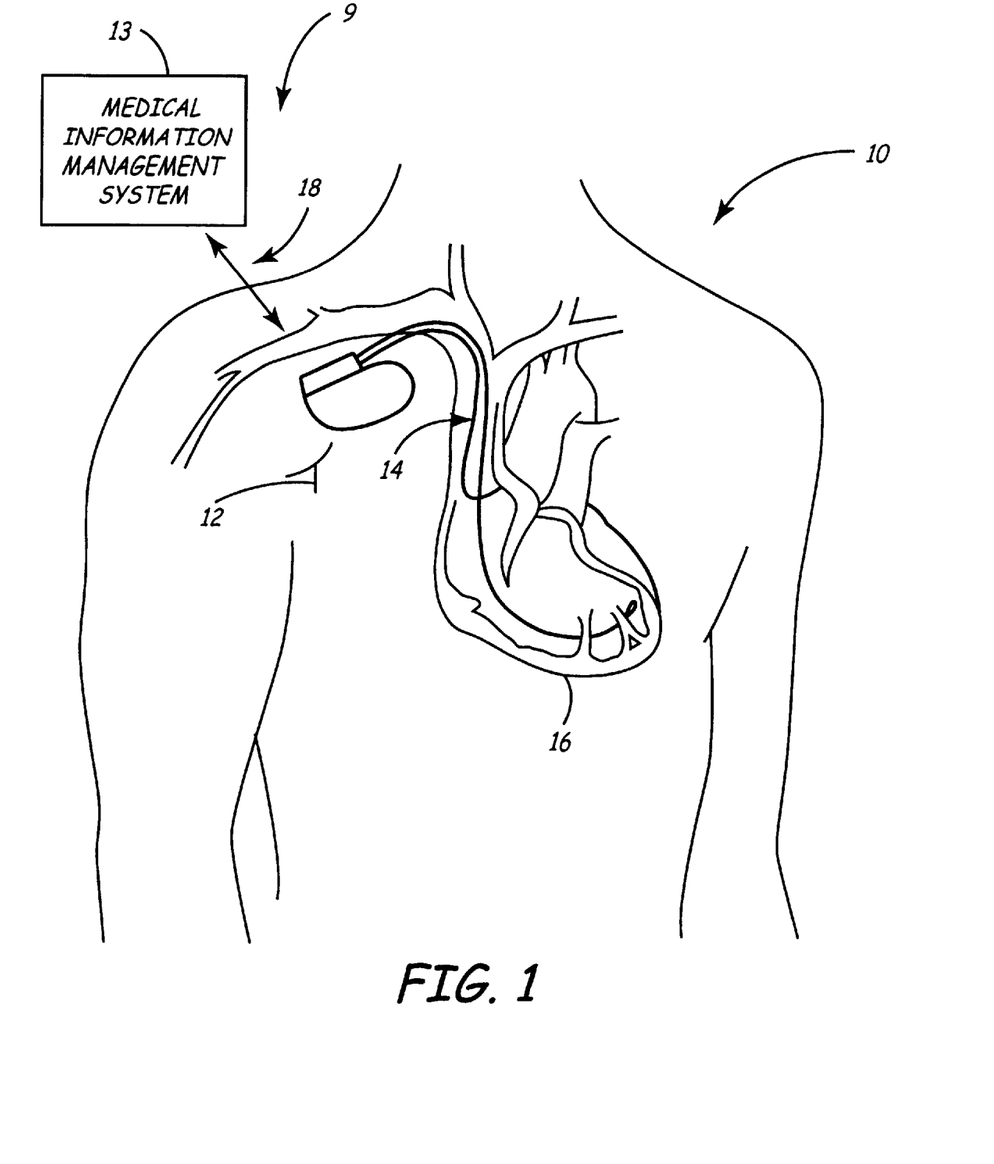
FIG. 1 is a diagram illustrating an implantable medical device communication system according to the present invention including an implantable medical device in a body for communication with a medical information management system.

FIG. 1 is a simplified schematic view of an implantable medical device communication system 9 according to the present invention. The implantable medical device communication system 9 includes an implantable medical device 12 for communication through a link 8 (including a module interface apparatus 15 shown in FIG. 3) with a medical information management system 13. The present invention leverages a medical information management system's infrastructure (e.g., computer subsystems, control stations, networks, print options, database management, operating systems, etc.) which are generally upgraded on a continuous basis with regard to hardware thereof. For example, such medical information management systems, as described further below, may be conventional monitoring systems such as a computer networked system in a hospital facility. Generally, for example, such a medical information management system 13 can be configured for acceptance of one or more interface modules, e.g., plug-in modules, for interfacing external devices to the medical information management system 13. The present invention uses the infrastructure of the medical information management system 13 to implement a programming apparatus for communication with an implantable medical device 12. For example, such communication may include both downlink communications, e.g., communication of programming commands to the implantable medical device 12, and uplink communications, e.g., communication of diagnostic/physiological parameter data, to the medical information management system 13.

As shown in FIG. 1, the implantable medical device 12 is implanted in a body 10 near a human heart 16. Implanted medical device 12 is electrically connected to the heart by leads 14. In the case where the implanted medical device 12 is a pacemaker, the leads 14 are pacing and sensing leads connected to the heart 16 from the implanted medical device 12. Such leads sense electrical signals attendant to the depolarization and repolarization of the heart 16 and provide pacing pulses for causing depolarization of cardiac tissue in the vicinity of the distal ends thereof. Implantable medical device 12 may be any implantable cardiac pacemaker such as those disclosed in U.S. Pat. No. 5,158,078 to Bennett et al.; U.S. Pat. No. 5,312,453 to Shelton et al.; or U.S. Pat. No. 5,144,949 to Olson.

Implantable medical device 12 may also be a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, implantable medical device 12 may be an implantable nerve stimulator or muscle stimulator such as that disclosed in U.S. Pat. No. 5,199,428 to Obel et al.; U.S. Pat. No. 5,207,218 to Carpentier et al.; U.S. Pat. No. 5,330,507 to Schwartz; or an implantable monitoring :device such as that disclosed in U.S. Pat. No. 5,331,966 issued to Bennett et al.

Further, for example, the implanted medical device 12 may be a defibrillator, a cardioverter-defibrillator, a brain stimulator, a gastric stimulator, a drug pump, a hemodynamic monitoring device, or any other implantable device that would benefit from a communication system according to the present invention as described herein. Therefore, the present invention is believed to find wide application for use with any form of implantable medical device. As such, a description herein making reference to any particular medical device is not to be taken as a limitation of the type of medical device which can benefit from and which can be employed with a communication system as described herein.

In general, the implantable medical device 12 may include a hermetically sealed enclosure that may include various elements such as an electrochemical cell (e.g., a lithium battery), circuitry that controls device operations and records rhythmic EGM episodes, telemetry transceiver antenna and circuitry that communicates with the module interface apparatus as further described herein. Generally, the implantable medical device 12 is implemented with a microprocessor-based architecture. However, electronic features and operations of the implantable medical device 12 may be implemented in discrete logic or as a microcomputer-based system, as would be readily apparent to one skilled in the art.

Figure 2:
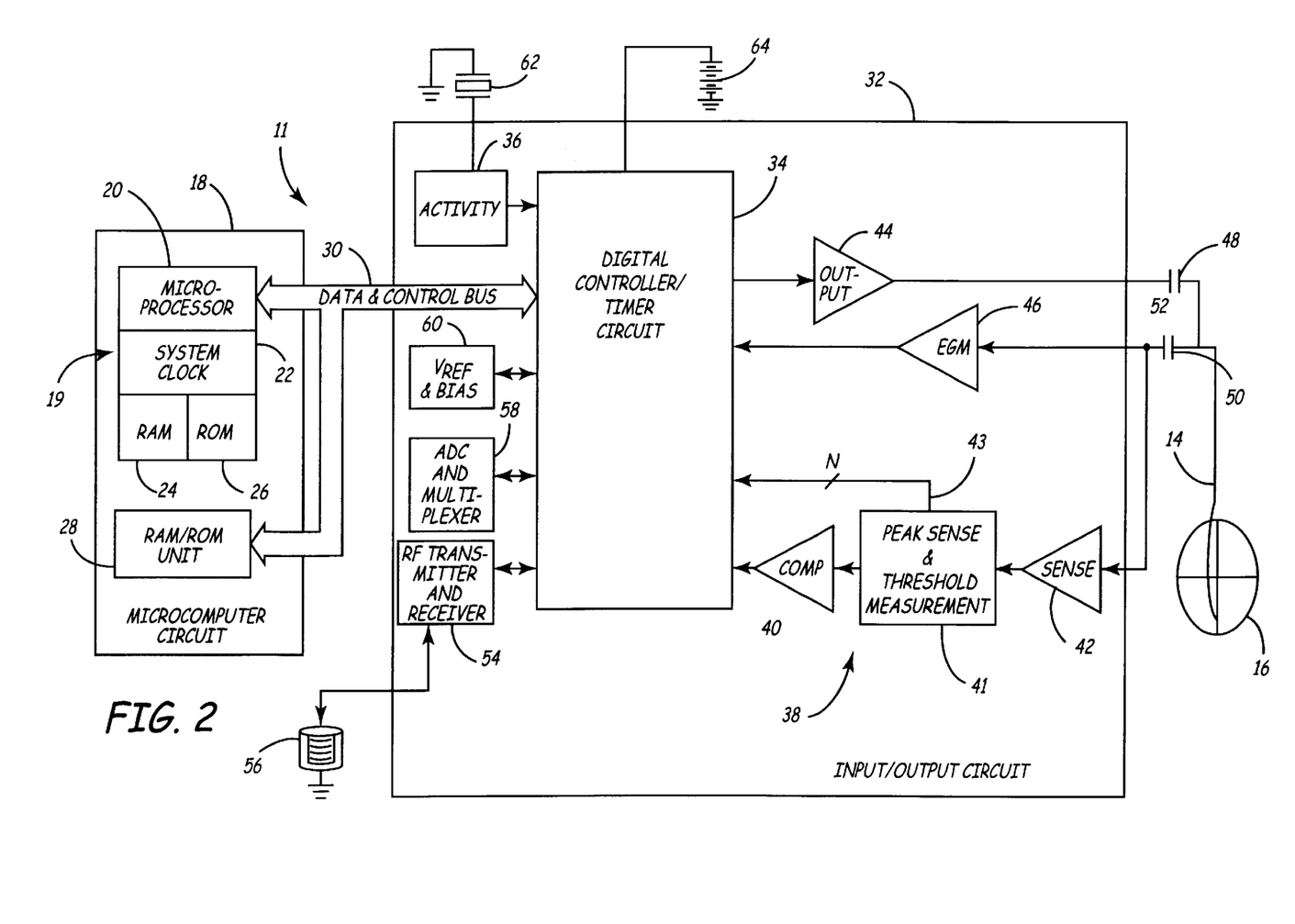
FIG. 2 is a general block diagram of circuitry of one embodiment of the implantable medical device of FIG. 1 including receiver and transmitter circuitry for use in communication according to the present invention.

FIG. 2 shows a block diagram illustrating components of a pacemaker 11 in accordance with one embodiment of the present invention where pacemaker 11 has RF transmitter and receiver circuitry 54 for communication via the pacemaker antenna 56 with the module interface apparatus 15 according to the present invention as further described herein. In the illustrative embodiment shown in FIG. 2, the pacemaker 11 is preferably programmable according to the present invention. Device antenna 56 is connected to input/output circuit 32 to permit uplink/downlink communication through RF device transmitter and receiver circuitry 54.

Pacemaker 11 illustratively shown in FIG. 2 is electrically coupled to the patient's heart 16 by lead 14 is coupled to a node 52 in the circuitry of pacemaker 11 through input capacitor 50. In the presently disclosed embodiment, an activity sensor 62 provides a sensor output to an activity circuit 36 of input/output circuit 32. Input/output circuit 32 also contains circuits for interfacing to heart 16, antenna 56, and contains circuits 44 for application of stimulating pulses to heart 16 to control its rate under control of software-implemented algorithms in microcomputer unit 18.

Microcomputer unit 18 preferably comprises on-board circuit 19 that includes microprocessor 20, system clock 22, and on-board random access memory (RAM) 24 and read-only memory (ROM) 26. In this illustrative embodiment, off-board circuit 28 comprises a RAM/ROM unit. On-board circuit 19 and off-board circuit 28 are each coupled by a communication bus 30 to digital controller/timer circuit 34.

The electrical components shown in FIG. 2 are powered by an appropriate implantable battery power source 64 in accordance with common practice in the art. For the sake of clarity, the coupling of battery power to the various components of pacemaker 11 is not shown in the figures.

$V_{REF}$ and bias circuit 60 generates a stable voltage reference and bias currents for circuits of input/output circuit 32. Analog to digital converter (ADC) and multiplexer unit 58 digitizes analog signals and voltages to provide "real-time" telemetry intracardiac and/or sensor signals and battery end-of-life (EOL) replacement function.

Operating commands for controlling the timing of pacemaker 11 are coupled by bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sense circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41 in turn provides an indication of peak sensed voltages and measured sense amplifier threshold voltages on path 43 to digital controller/timer circuit 34. An amplified sense amplifier signal is also provided to comparator/threshold detector 40. Sense amplifier 42 may, for example, correspond to that disclosed in U.S. Pat. No. 4,379,459 to Stein.

Circuit 34 is further preferably coupled to electrogram (EGM) amplifier 46 for receiving amplified process signals sensed by an electrode disposed on lead 14. The electrogram signal provided by EGM amplifier 46 is employed when the implanted device is being interrogated by an external programming apparatus to transmit by uplink telemetry a representation of an analog electrogram of the patient's electrical heart activity. Such functionality is, for example, shown in U.S. Pat. No. 4,556,063 to Thompson et al.

Output pulse generator 44 provides pulsing stimuli to the patient's heart 16 through coupling capacitor 48 in response to a pacing trigger signal provided by digital controller/timer circuit 34. Output amplifier 44, for example, may correspond generally to the output amplifier disclosed in U.S. Pat. No. 4,476,868 to Thompson.

Figure 3:
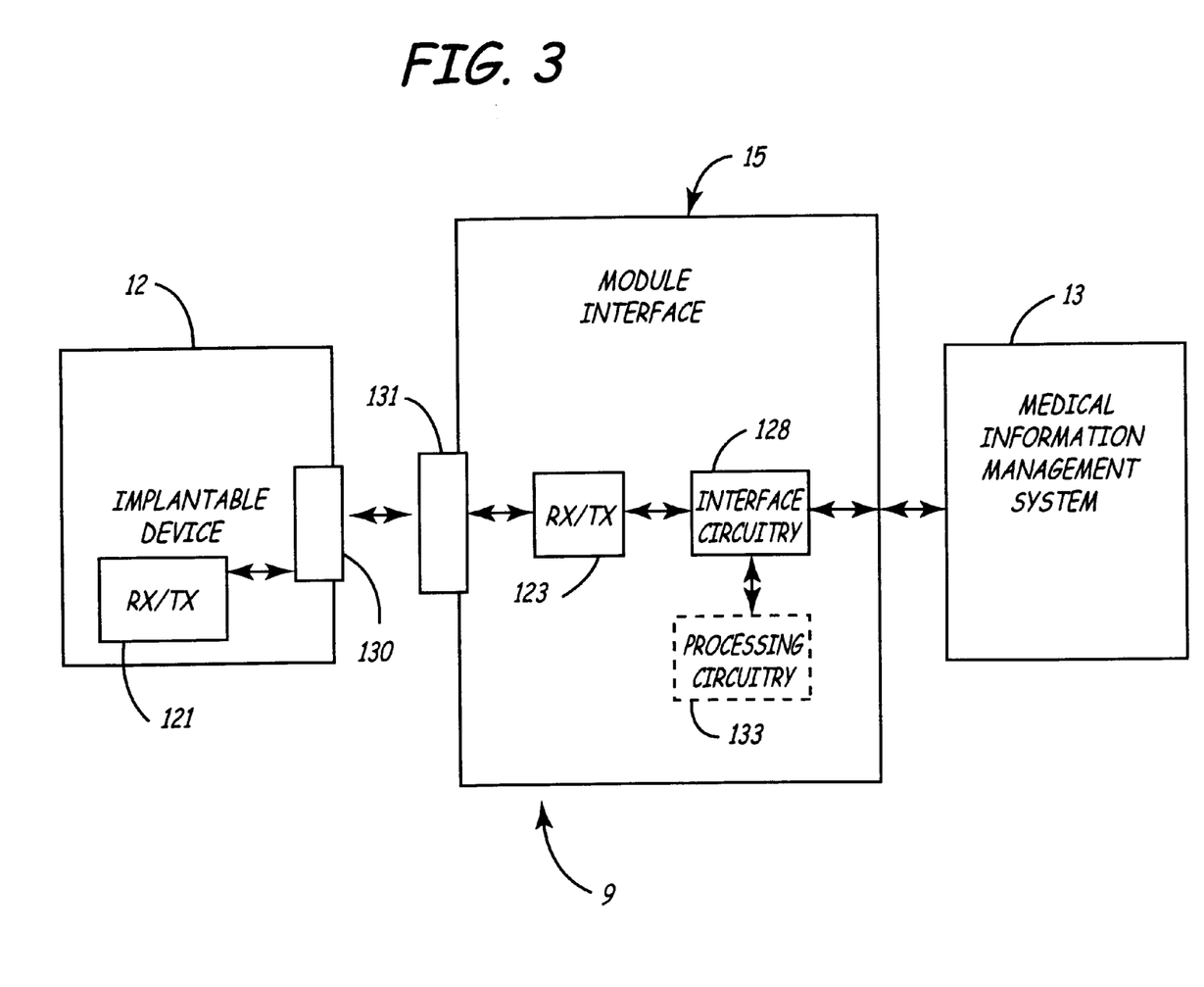
FIG. 3 is a general block diagram of the communication system of FIG. 1 according to the present invention using a module interface apparatus for communication between the implantable medical device and the medical information management system.

FIG. 3 is a block diagram of the implantable medical device communication system 9 according to the present invention. The implantable medical device communication system 9 includes the implantable medical device 12, a medical information management system 13, and a module interface apparatus 15. The implantable medical device 12 may include any implantable medical device such as those previously described herein. According to the present invention, the implantable medical device 12 includes transmitter and/or receiver circuitry 121 for use in communication of information between the implantable medical device 12 and the medical information management system 13. It will be recognized by one skilled in the art that the implantable medical device 12 may include a receiver, a transmitter, or both depending upon whether uplink, downlink, or a combination of uplink and downlink channels for the communication of information between the implantable medical device 12 and the medical information management system 13 are to be established.

Generally, implantable medical device 12 may receive programming commands from an external device positioned external to the skin of the patient. Such programmer command instructions are referred to herein as downlink transmissions, i.e., transmissions to the implantable medical device 12. For example, received programming commands may include program instructions or steps for directing the operation of the implantable medical device 12. Further, for example, the received command instructions may also include data such as program limits and timing data. Similarly, the implantable medical device 12 may transmit data external to the skin of the patient. Such transmissions are referred to herein as uplink transmissions, i.e., transmissions from the implantable medical device 12. In other words, the implantable medical device transmits data as well as receives data. Generally, implanted medical device 12 includes receiver and transmitter circuitry 121 which cooperate with other circuitry of the implanted medical device 12 to receive information via a device antenna 130 and to transmit data via the device antenna 130.

Medical information management system 13 refers generally to a system operable for receiving information from one or more external devices with the capability of processing such data. Preferably, according to the present invention, the medical information management system 13 is operable with a plug-in module interface architecture. Preferably, the plug-in module interface architecture includes hardware for receiving a plurality of interface modules such that medical products which provide digital and/or analog outputs can be integrated, i.e., interfaced, to the medical information management system 13. Generally, the medical information management system 13 at a minimum includes a computer processing system for providing processing capabilities relative to information received from the implantable medical device 12. Further, preferably, the medical information management system 13 includes a user interface (e.g., keyboard, mouse, touch screen, and associated software interface such as a Windows-based interface) associated with a display unit for use in providing programming for the implantable medical device 12. One skilled in the art will recognize that any number of different peripherals may be components of the medical information management system 13. Preferably, the medical information management system 13 includes at least a processor, a communication network, storage media, a printer/plotter, and a display.

Figure 6:
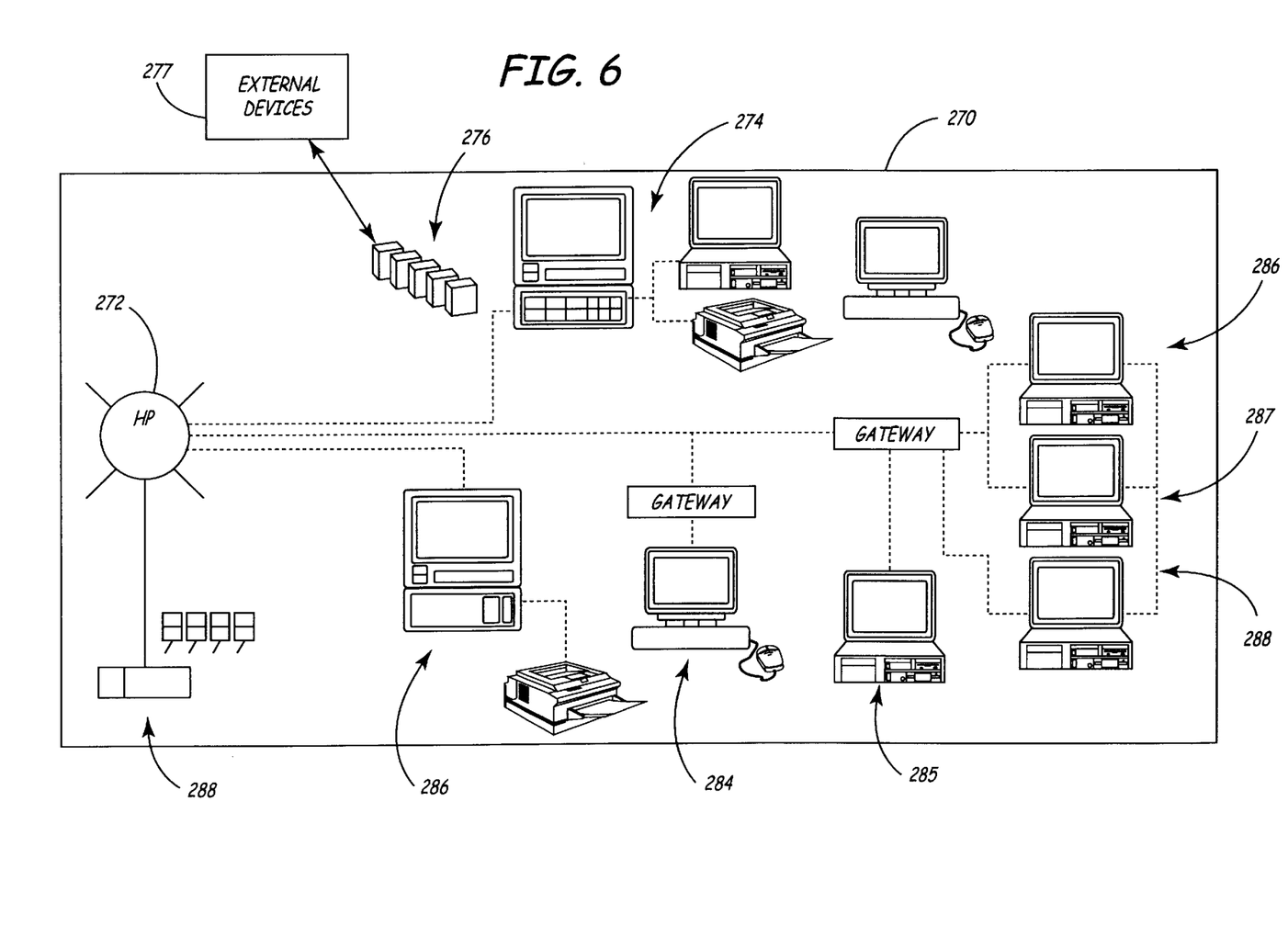
FIG. 6 is one illustrative embodiment of a medical information management system for use in the system of FIG. 3 including a computer network according to the present invention.
Figure 7:
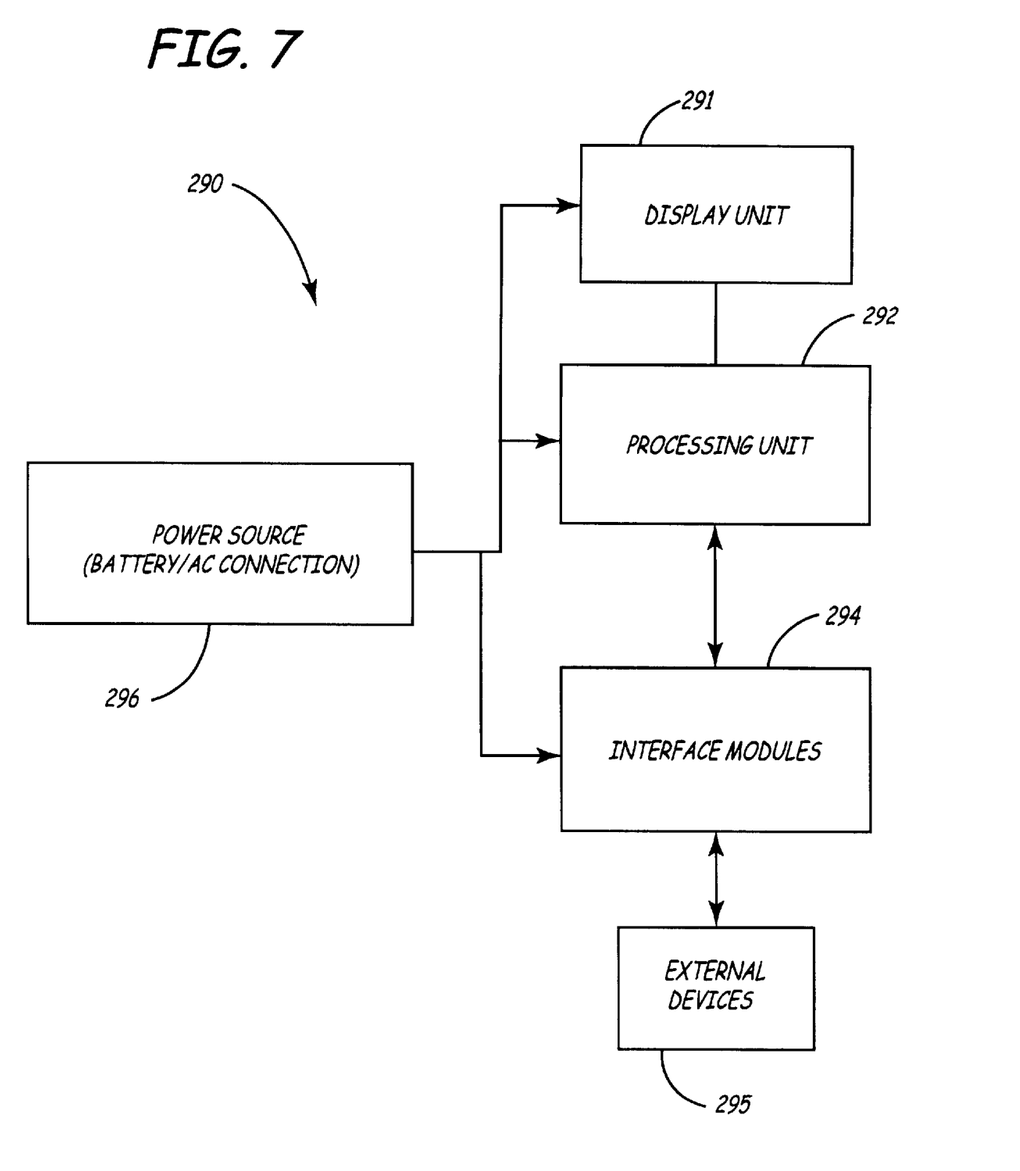
FIG. 7 is an alternate medical information management system for use in the system of FIG. 3 wherein the medical information management system includes a portable battery operable computer processing system.

FIGS. 6 and 7 show two embodiments of illustrative medical information management systems 13. FIG. 6 shows a networked medical information management system 270 and FIG. 7 shows a portable battery operable medical information management system 290.

The networked medical information management system 270 as shown in FIG. 6 includes one or more computer processing subsystems (e.g., component monitoring system 274) connected to a computer network represented generally as controlled network 272. Generally, such a system 270 is utilized in larger medical facilities. Further, other gateways to the controlled network 272 are provided for various functionality of the networked medical information management system 270. For example, digital telemetry subsystem 288 may be used to provide telemetry to the network 272; a component control manager subsystem 286 may provide for control of various components of the network 272; and various other subsystems 284–288 may provide for various other functions connected to the network, such as alarm systems, hospital patient archival records, laboratory information databases, remote access terminals, etc. One skilled in the art will recognize that various configurations and components of the networked system 270 are possible and that the illustrative FIG. 6 is but one of an unlimited number of configurations possible for such a system 270.

Preferably, the networked medical information management system 270 includes at least one component monitoring system 274 (e.g., a computer processing subsystem) wherein the system interacts with a plurality of module interfaces 276. Each of the module interfaces 276 is operable for use in communication of information between an external device 277 corresponding to a module interface and the networked medical information management system 270. For example, the external devices 277 may include devices such as a ventilator, a gas analyzer, a temperature sensor, or any other device external to the body that provides an analog and/or digital output which can be interfaced to the networked medical information management system 270 through the plurality of module interfaces 276.

As described above, such a networked medical information management system 270 may include any number of different components, and a listing of the peripherals or components attached to the network 272 are not limited by any of those listed herein. For example, the networked medical information management system 270 may include various computer subsystems, various types of networks, remote modem connections, distributed hospital/clinic connections, database systems, various portable devices, battery back-ups, generators, etc.

Various types of already existing infrastructures for networked medical information management systems 270 are available. For example, a networked medical information management system 270 or components thereof are described in U.S. Pat. No. 5,520,191 to Karlsson et al., entitled "Myocardial Ischemia And Infarction Analysis And Monitoring Method And Apparatus"; U.S. Pat. No. 5,687,734 to Dempsey et al., entitled "Flexible Patient Monitoring System Featuring A Multiport Transmitter"; U.S. Pat. No. 5,417,222 to Dempsey et al., entitled "Patient Monitoring System"; and U.S. Pat. No. 5,579,775 to Dempsey et al., entitled, "Dynamic control Of A Patient Monitoring System." Preferably, according to the present invention, the networked medical information management system 270 includes the utilization of the Hewlett Packard Component Monitoring System (CMS) available under the trade designation Viridia CMS which with its associated display unit (e.g., flat screen or CRT color monitor) can be networked to a computer network. Further, preferably, the plurality of interface modules 276 for interfacing various external devices 277 are provided through the use of a plug-in interface available from Hewlett Packard under the trade designation of HP VueLink Interface. Detailed information with regard to the Hewlett Packard CMS and Hewlett Packard VueLink Interface is available from Hewlett Packard Company, Palo Alto, Calif.

Generally, the Hewlett Packard CMS is an open architecture system which allows for use of specific functions to be integrated into a Hewlett Packard network and database system. For example, it is possible to provide software on the network for controlling external devices or for receiving information from external devices via the plug-in module open architecture. Such software according to the present invention would provide for the programming of the implantable medical device 12 and/or monitoring of the patient or device implanted therein. The Hewlett Packard CMS is a Windows NT-based system. As the above Hewlett Packard products are commercially available, further details with regard to the system shall not be provided herein for simplicity purposes.

FIG. 7 shows the portable battery operable medical information management system 290 for use according to the present invention. The portable medical information management system 290 includes a display unit 291 and processing unit 292 which may be powered by a power source 296 that is either battery operated or has a connection to an AC power source, e.g., power cord connection. Further, the battery operable system 290 is operable with one or more interface modules 294 for interfacing various external devices 295, such as those described above, to the processing unit 292. Such a portable or smaller system, for example, may generally be used in a satellite office or in transport of a patient, or, further, for example, in a smaller medical facility.

Preferably, according to the present invention, the portable, battery operable medical information management system 290 is a system available from Hewlett Packard under the trade designation HP-M1275A Component Transport System (CTS). Generally, the Hewlett Packard CTS is a system 290 that is a flexible and transportable patient monitoring system based on a variety of components that enable customization to a hospital's requirements. For example, the Hewlett Packard system includes a transport mainframe that contains the display unit and processing capabilities. The system utilizes the same type of interface modules as the HP CMS, which is described in general above with regard to the networked medical information management system 270.

Both the HP CMS and CTS systems have similar operator controls and waveform display. A computer subsystem is responsible for parameter processing, display control, and interfacing. The same types of interface modules are receivable in plug-in slots of the component transport system, i.e., the HP VueLink Interface plug-in receiving unit is usable for both the HP CMS and CTS. Some patient-related settings may even be transferred between the CMS and the CTS via an interface module, and vital signs, may, for example, be transferred through such transfer modules.

Generally, the interface modules 294, are contained in a separable rack, but the rack is designed to dock with the monitor mainframe which eliminates extra cable requirements. This same type of HP VueLink slot rack can be used for the, Hewlett Packard CMS and the CTS.

As described above, one skilled in:the art will recognize that the medical information management system 13 according to the present invention is preferably a system including the ability to implement software for providing program commands for communication to an implantable medical device and for receiving data and displaying data from the implantable medical device 12, e.g., diagnostic data, physiological parameter data, histograms, counters, trend plots, etc., and preferably processing such data. It will be recognized that in the case of the networked medical information management system 270, monitoring or control of programming may be performed from any node on the network. Further, preferably, the medical information management system 13 is configured for receiving a plurality of interface modules for interfacing to corresponding external devices, e.g., ventilators, gas analyzers, etc. For example, with regard to the Hewlett Packard CMS and the Hewlett Packard CTS, such a configuration is provided with use of the Hewlett Packard VueLink Interface.

Preferably, such a configuration includes a plug-in module rack. However, one skilled in the art will recognize that data may be transmitted over a variety of mediums. Therefore, a plug-in rack may not be necessary as in the case of information provided to the medical information management system 13 via a modem connection. The present invention leverages the infrastructure of a medical information management system 13, preferably, a commercially available system whose hardware is continually upgraded. Such leverage is attained by providing a module interface apparatus 15, e.g., a plug-in module that is compatible with the Hewlett Packard VueLink Interface, to interface the implantable medical device 12 to the medical information management system 13. Through the use of the module interface apparatus 15, communication of programming commands from the medical information management system 13 to the implantable medical device 12 can be performed. Further, the module interface apparatus 15 provides for communication of device data from the implantable medical device 12 to the medical information management system 13.

This configuration for the implantable medical device communication system 9 reduces the need for a standalone programming apparatus as previously described in the Background of the Invention section herein. In such a configuration of an implantable medical device communication system 9, the module interface apparatus 15 provides the link 8 between the implantable medical device 12 and the medical information management system 13 and piggybacks on the natural progression of such a medical information management system 13. For example, as the medical information management system 13 is upgraded, such upgrades are passed through to the programming communication system according to the present invention without the necessary incorporation of technological advances in a conventional standalone programming apparatus. As such, this reduces the need to continually upgrade the operating system, print options, database management systems, connectivity requirements, etc. with respect to the integrated programming apparatus according to the present invention. This is unlike a standalone programmer apparatus which would require such continual upgrades. Further, data is available for input directly into a patient's record in the medical information management system 13 without the need for transfer of such data from a standalone programmer which conventionally in some circumstances needed to be done manually with possibility of error.

Generally, the module interface apparatus 15 shown in FIG. 3 includes at least transmitter/receiver circuitry 123 and an interface antenna 131 for transmitting and receiving electromagnetic energy. The module interface apparatus 15 includes receiver circuitry that is compatible with the transmitter of the implantable medical device 12 and operable for receiving and extracting, e.g., demodulating, data from the transmitted signal from the implantable medical device 12. Further, the module interface apparatus 15 includes transmitter circuitry that is compatible with the receiver of the implantable medical device 112 and operable for generating a modulated signal of which the receiver of the implantable medical device 112 is capable of receiving and extracting e.g., demodulating, information therefrom.

Generally, the implantable medical device communication system 9 may be used for communication of information to the implantable medical device 12 or from the implantable medical device 12. In the case of providing programming commands to the implantable medical device 12, data representative of programming commands is received at the module interface apparatus 15. The medical information management system 13 includes the necessary operating system, user interface, database management, and any software necessary and compatible with the programming requirements of the implantable medical device 12 to provide the appropriate programming commands to the module interface apparatus 15. The module interface apparatus 15 includes interface circuitry 128 to adapt the programming data for transmission by the transmitter/receiver circuitry 123 to the implantable medical device 12. The data representative of the programming commands is adapted by the interface circuitry 128 and provided to the interface transmitter of the receiver/transmitter circuitry 123.

The adaptation of the data representative of the programming commands by the interface circuitry 128 may include any number of operations, such as for example, amplification, processing, conditioning, parallel to serial conversion, data buffering, error detection and correction, data encryption/encoding, data compression, telemetry link management and channel management, operational status (e.g., module status lights, warnings indicators, etc.) and any other operation necessary as determined by the type of telemetry used between the transmitter of the module interface apparatus 15 and the receiver of the implantable medical device 12. The adapted data representative of the programming commands is then transmitted via the interface antenna 131 of the module interface apparatus 15 to the implantable medical device 12 where it is received at the device antenna 130 and detected by device receiver/transmitter circuitry 121.

Likewise, device data may be provided by the implantable medical device 12 to the medical information management system 13 through the module interface apparatus 15. Device data may include any type of data provided by an implantable medical device including real-time and stored data, such as diagnostic data (e.g., data for patient diagnosis or implanted device function diagnosis), physiological parameter data (e.g., oxygen sensed levels, activity sensor data, ECG waveforms and data, etc.), operational data (e.g., lead impedance data, battery voltage data, etc., and analyzed data (e.g., variability plot data, trend data, etc.). Data is transmitted by the device transmitter of transmitter/receiver circuitry 121 via the device antenna 130. The electromagnetic energy is received at the interface antenna 131 of the module interface apparatus 15 and a received signal is provided to the receiver of the receiver/transmitter circuitry 123 for detection and extraction of transmitted data from the signal. Upon extraction of the data by the interface receiver of the transmitter/receiver circuitry 123, the interface circuitry 128 of the module interface apparatus 15 adapts the data for provision to the medical information management system 13. For example, such adaptation may include amplification, conditioning, processing, serial to parallel conversion of the stream of data, data management/formatting, data compression, data encryption, report generation, data buffering, error detection/correction, or any other any other operation necessary as determined by the type of telemetry used between the receiver of the module interface apparatus 15 and the transmitter of the implantable medical device 12. The adapted data representative of the device data received via the interface antenna 131 is then provided to the medical information management system 13.

Further, more extensive processing may be performed in the module interface apparatus 15 upon operation of optional processing circuitry 133. For example, the processing circuitry 133 may act upon the device data received from the implantable medical device 12 to provide a sampled amount of data, to provide data representative of a physiological parameter based upon multiple sensor outputs signals, to provide an alarm status upon operation of detection circuitry for detecting a warning event, and to provide operational status indication (e.g., status lights to indicate proper telemetry function, programming confirmation, etc.) The adapted data is then provided to the medical information management system 13.

The communication of data from the module interface apparatus 15 to the medical information management system 13 may be accomplished in a number of manners. For example, in conjunction with the use of a plug-in module such as used. in the HP VueLink Interface for the HP CMS and CTS equipment, the transfer of data between the module interface apparatus 15 and the medical information management system 13 may be accomplished by a direct electrical line, e.g., Local Area Network (LAN) or Wide Area Network (WAN). However, various other methods of transport may be used as well, such as RF transmission, or any other wireless technologies, modem technologies, infrared technologies, optical technologies, etc.

In its simplest form for the transmission of programming information to the implantable medical device 12, the module interface apparatus 15 includes an interface antenna 131 for transmitting electromagnetic waves to the device antenna of the implantable medical device and an interface transmitter that is compatible with the device receiver of the implantable medical device 12. In other words, for example, the modulation and demodulation techniques and operating frequencies of the corresponding device receiver and module interface transmitter are compatible. Likewise, for transmission from the implantable medical device 12 to the module interface apparatus 15, the device transmitter of receiver/transmitter circuitry 121 is compatible with the interface receiver of receiver/transmitter circuitry 123 of the module interface apparatus 15. In other words, for example, the modulation and demodulation techniques and operating frequencies of the corresponding device transmitter and the interface module receiver are compatible.

Figure 4:
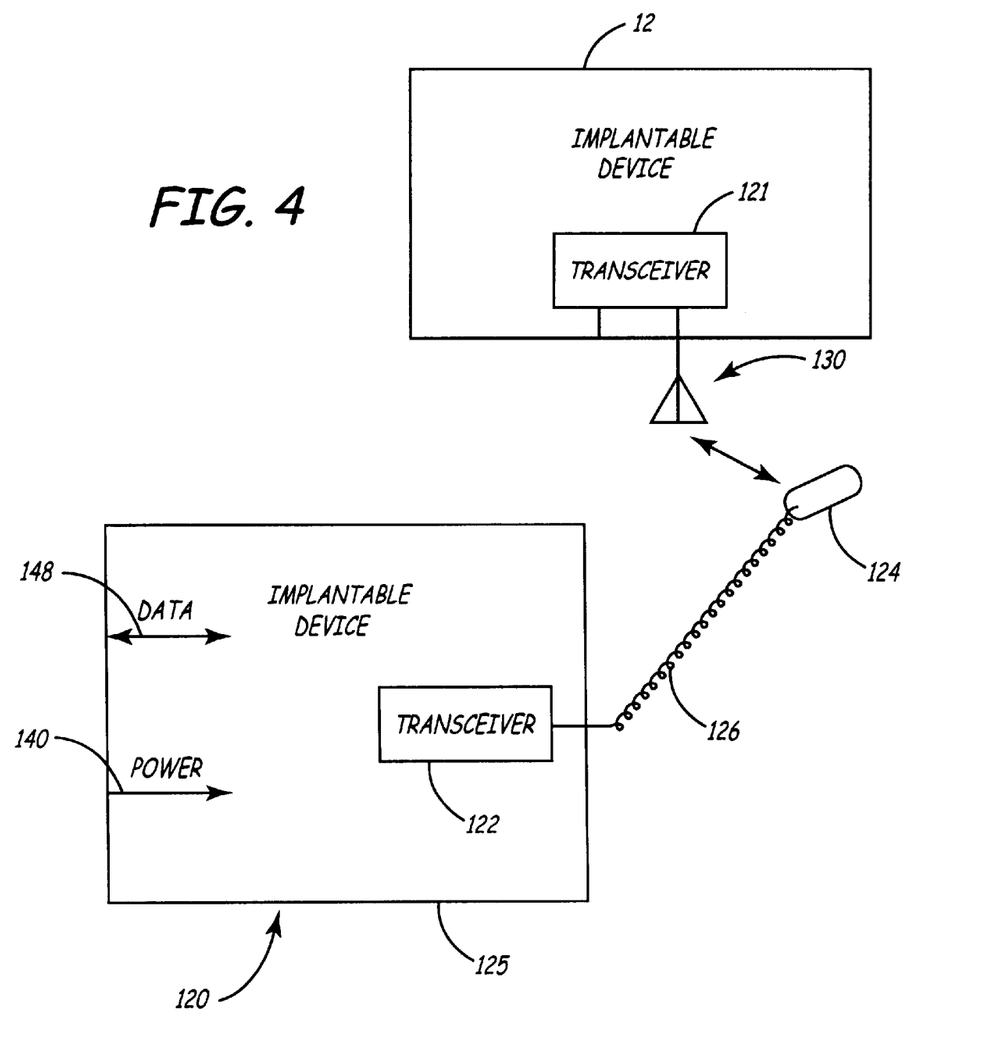
FIG. 4 is one embodiment of the module interface apparatus of FIG. 3 in communication with an implantable medical device according to the present invention.
Figure 5:
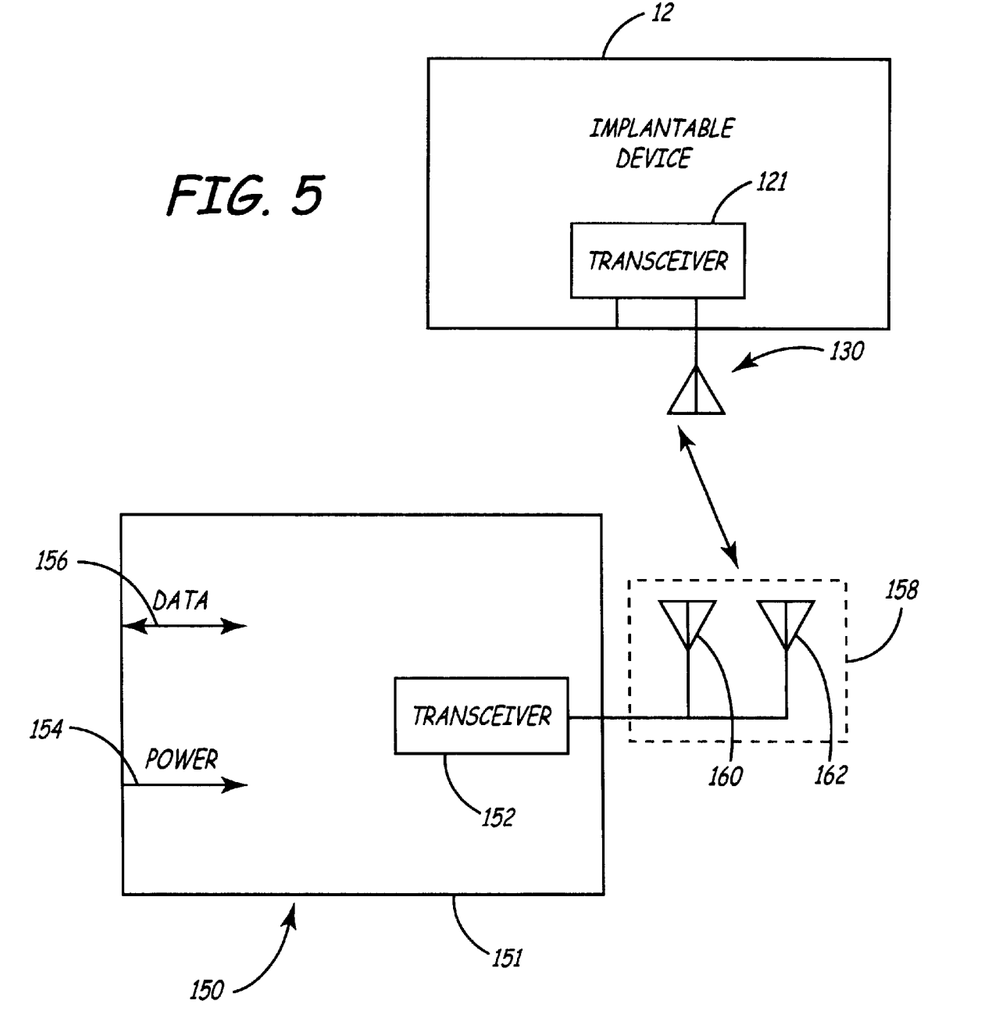
FIG. 5 is an alternate embodiment of the module interface apparatus of FIG. 3 in communication With an implantable medical device according to the present invention.

Two illustrative embodiments of the module interface apparatus are illustrated in FIGS. 4 and 5. However, various systems for performing telemetry between the implantable medical device 12 and module interface apparatus 15 may be used and are known. For example, several of such systems are described in U.S. Pat. No. 5,127,404 issued to Wyborney et al.; U.S. Pat. No. 4,556,063 issued to Thompson et al.; and U.S. Pat. No. 5,342,408 issued to De Coriolis et al.

As shown in FIG. 4, module interface apparatus 120 includes an interface module 125 including a module housing which contains transceiver circuitry 122 and any other circuitry such as previously described herein. The module interface apparatus 120 further includes an antenna positioned within a programmer head 124 connected to the transceiver circuitry 122 via a stretchable cable 126 and is powered by source 140. Further, data 148 is communicated to the medical information management network 13. Wireless communication and/or any other electrical connection may be possible between the programmer head and the interface module 121. The programmer head 124 containing the antenna may then be positioned at the implant site relative to device antenna 130 and the implantable medical device 12 which contains the transceiver circuitry 121. Such an interface may be used in conjunction with telemetry according to U.S. Pat. No. 5,527,348; a low frequency (175 kHz), near field (3–4 inches), and low data rate (4–50k baud) telemetry system.

FIG. 5 provides an alternate module interface apparatus 150. The module interface apparatus 150 includes interface module 151 which has a module housing to contain the transceiver circuitry 152 and any other circuitry of the apparatus 150 such as described previously herein. Power is applied by power source 154 and data 156 is communicated to the medical information management system 13. The transceiver circuitry 152 is connected to one or more antennas 158, represented by antenna elements 160, 162. Communication may then be performed via the device antenna 130 and the implantable medical device 12 which contains the transceiver circuitry 121. In this case, a programmer head is unnecessary and telemetry is generally accomplished using a system such as described in U.S. Pat. No. 5,683,432; a high frequency (400 MHz), far field (to 30 feet), and high data rate (to 100k baud) telemetry system.

All patents and references cited herein are incorporated in their entirety as if each were incorporated separately. This invention has been described with reference to illustrative embodiments and is not meant to be construed in a limiting sense. As described previously, one skilled in the art will recognize that various other telemetry techniques for providing communication between an implantable medical device and module interface apparatus may be used in addition to those previously described herein. Further, various modifications of the illustrative embodiments, as well as additional embodiments of the invention, will be apparent to a person skilled in the art upon reference to this description.

What is claimed is:

1. A system for communication with an implantable medical device, comprising:
   an implantable medical device having a data transceiver for uplink of operational data and acceptance of down-linked program command data;
   a medical information system having a computer processing unit and a display unit, said computer processing unit including software providing program command data for communication to the implantable medical device and accepting data and displaying data produced by the implantable medical device; and
   an interface module coupled to the medical information system and having a transceiver for data communication with the implantable medical device;
   said interface module including interface circuitry operable to adapt the program command data provided by the medical information management system for communication to the implantable medical device, said interface circuitry further operable to adapt operational data received from the implantable medical device for communication to the medical information management system.

2. The system of claim 1 wherein the implantable medical device is a cardiac pacemaker.

3. The system of claim 1 wherein the implantable medical device is a cardiac pacemaker-cardioverter-defibrillator (PCD).

4. The system of claim 1 wherein the operational data up-linked from the implantable medical device comprises data selected from a group consisting of diagnostic data, physiological parameter data, device operational data, analyzed data, and histogram data.

5. The system of claim 1 further comprising a plurality of additional interface modules coupled to the medical information system, each of said additional interface modules interfacing to an external device.

6. The system of claim 1 wherein the interface circuitry adapts the program command data by performing an operation selected from a group consisting of data encryption/encoding, data compression, and error detection.

7. The system of claim 1 wherein the medical information system includes a controlled network.

8. The system of claim 7 wherein the medical information system includes a plurality of plug-in interface modules interfaced to a plurality of external devices and a computer processing subsystem having software for controlling the external devices.

9. The system of claim 8 wherein the external devices is selected from a group consisting of a ventilator, a gas analyzer, and a temperature sensor.

10. The system of claim 7 wherein the medical information system includes a plurality of computer processing subsystems that obtain access to the controlled network by gateways.

11. The system of claim 10 wherein one of the computer processing subsystems provides patient archival records.

12. The system of claim 10 wherein one of the computer processing subsystems is a remote access terminal.

13. The system of claim 10 wherein one of the computer processing subsystems provides a laboratory information database.

14. A system for communication with an implantable medical device having a data transceiver for uplink of operational data and acceptance of down-linked program command data, comprising:
   a medical information system comprising a controlled network and a plurality of computer processing subsystems that access the controlled network; and
   a plurality of plug-in interface modules interfaced to a plurality of external devices, one of said plug-in interface modules having a transceiver for data communication with the implantable medical device;
   wherein one of the computer processing subsystems of the medical information system accessing the controlled network includes software for controlling the external devices interfaced to the plug-in interface modules;
   wherein one of the computer processing subsystems of the medical information system accessing the controlled network includes software providing information comprising a patient archival record database; and
   wherein one of the computer processing subsystems of the medical information system accessing the controlled network includes software for controlling communication to the implantable medical device.

15. The system of claim 14 wherein the computer processing subsystem for controlling communication to the implantable medical device provides data for programming of the device.

16. The system of claim 14 wherein the computer processing subsystem for controlling communication to the implantable medical device accepts data for monitoring the device.

* * * * *

UNITED STATES PATENT AND TRADEMARK OFFICE
CERTIFICATE OF CORRECTION

PATENT NO.   : 6,477,424 B1
DATED        : November 5, 2002
INVENTOR(S)  : David L. Thompson et al.

It is certified that error appears in the above-identified patent and that said Letters Patent is hereby corrected as shown below:

<u>Title page,</u>
Item [57], ABSTRACT,
Line 19, delete "information to:the" and insert -- information to the --.

Signed and Sealed this

Thirtieth Day of May, 2006

JON W. DUDAS
*Director of the United States Patent and Trademark Office*